(12) United States Patent
Pagedas

(10) Patent No.: US 6,221,384 B1
(45) Date of Patent: Apr. 24, 2001

(54) SEGMENTED TRANSDERMAL DOSAGE UNIT

(76) Inventor: Anthony C. Pagedas, 8401 W. Edgerton, Greendale, WI (US) 53129

( * ) Notice: Subject to any disclaimer, the term of this patent is extended or adjusted under 35 U.S.C. 154(b) by 0 days.

(21) Appl. No.: 09/434,227

(22) Filed: Nov. 5, 1999

(51) Int. Cl.[7] .............................. A61K 9/70; A61F 13/02
(52) U.S. Cl. ............................................ 424/449; 424/448
(58) Field of Search .................................... 424/448, 449; 206/532; 604/897

(56) References Cited

U.S. PATENT DOCUMENTS

| | | | |
|---|---|---|---|
| 4,666,441 | * 5/1987 | Andriola et al. | 604/897 |
| 4,883,669 | 11/1989 | Chien et al. | 424/448 |
| 4,906,169 | 3/1990 | Chien et al. | 424/448 |
| 5,046,618 | * 9/1991 | Wood | 206/532 |
| 5,145,682 | 9/1992 | Chien et al. | 424/448 |
| 5,756,117 | * 5/1998 | D'Angelo et al. | 424/449 |

FOREIGN PATENT DOCUMENTS

| | | |
|---|---|---|
| 0335231 | 10/1989 | (EP) . |
| 0559411 | 9/1993 | (EP) . |
| 2162422 | 2/1986 | (GB) . |
| 2184019 | 6/1987 | (GB) . |

OTHER PUBLICATIONS

Advertisement page: Esclim—estradiol transdermal system.

* cited by examiner

Primary Examiner—Thurman K. Page
Assistant Examiner—B. Fubara
(74) Attorney, Agent, or Firm—Ryan Kromholz & Manion, S.C.

(57) ABSTRACT

A dermal or transdermal segmented dosage unit for administering a dosage of a pharmaceutical to the skin of a patient. The dosage unit of this invention includes a backing layer which is non-permeable with respect to a pharmaceutical to be administered by the dosage unit, a membranous layer that is permeable to the pharmaceutical, a biologically acceptable adhesive, an impermeable coating means for dividing and severing the dosage unit into pre-selected segmental areas corresponding to fractional dosages of pharmaceutical. The fractional dosages may be administered in any pre-selected combination.

9 Claims, 3 Drawing Sheets

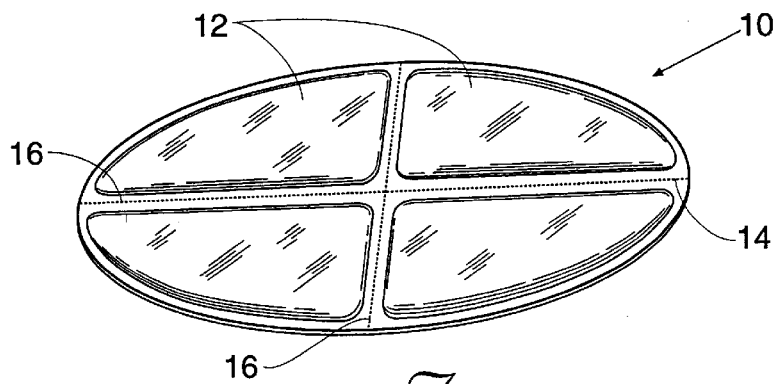
Fig. 1
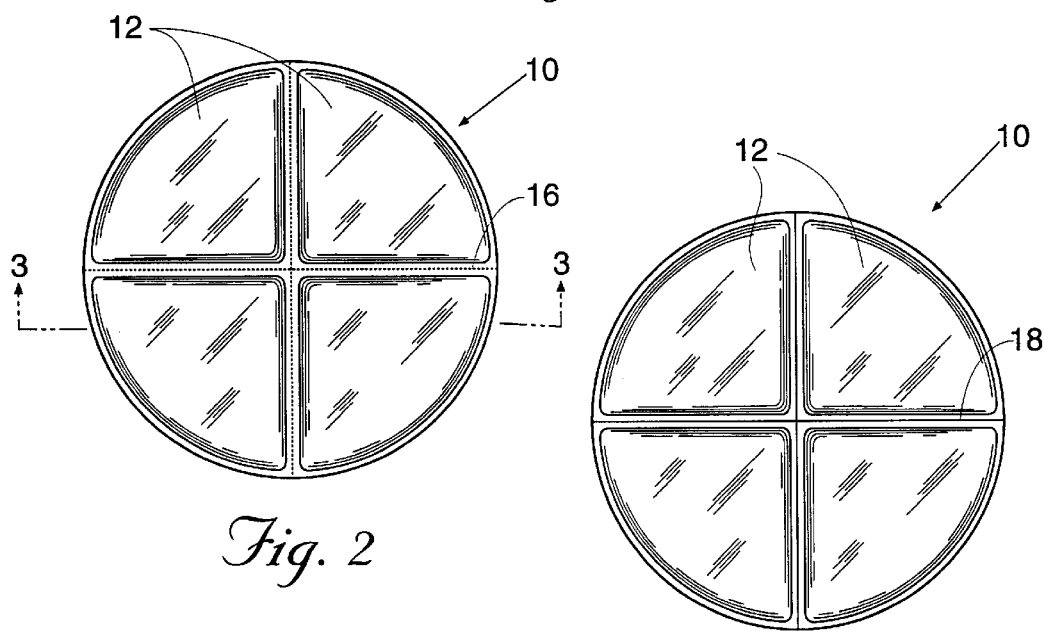
Fig. 2
Fig. 2a
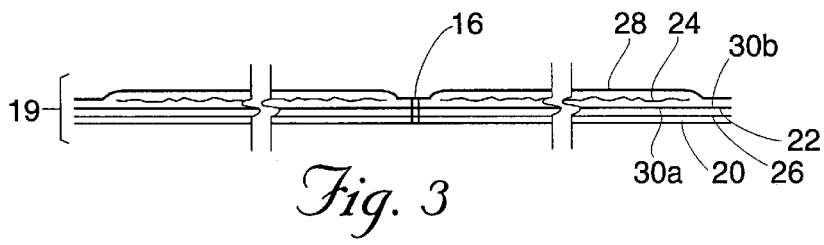
Fig. 3
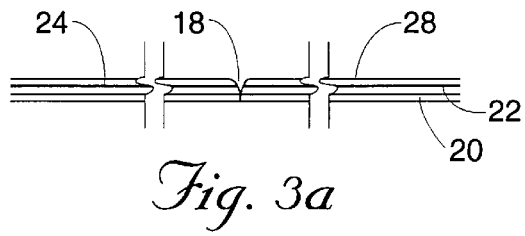
Fig. 3a

SEGMENTED TRANSDERMAL DOSAGE UNIT

BACKGROUND OF THE INVENTION

Transdermal absorption dosage units have been developed for use with a variety of pharmaceutical products, including beta-blockers, estrogen replacements, and nitroglycerin. An example of a dosage unit has been disclosed in U.S. Pat. No. 4,666,441 granted to Andriola et al. As disclosed therein, a dermal or transdermal patch includes a compartmentalized layer containing at least one drug or drug formulation within a respective compartment. The walls separating adjoining compartments are burstable thus allowing the respective pharmaceuticals of each adjoining compartment to be mixed or worked together by the user prior to applying the patch. Typically, transdermal absorption dosage units comprise a number of layers including a removable backing layer, an adjoining layer including a dosage of a pharmaceutical, a biologically acceptable adhesive means and an impermeable coating. During treatment, a heath care professional selects the appropriate dosage from an array of prepackaged dosage units. Each dosage requires a different dosage unit selection. Hence, a medical professional may prescribe a particular dosage unit for a patient, but if the dosage is inadequate, either by providing too high or low a dosage for that particular individual, the patient must buy an additional supply of the new dosage. This can be costly and wasteful to the patient, as dosage units in the unsatisfactory dosage level are left unused. Further, this procedure is time consuming for both the medical professional and the patient, particularly in cases in which the dosage must be modified and monitored over time to achieve the optimal dosage result for a particular individual. In those instances, the medical professional must rewrite a prescription for the patient to refill each time a different dosage is to be tried.

SUMMARY OF THE INVENTION

In view of the above-noted concerns, and also to present a dosage unit that is not rupturable to permit mixing of pharmaceutical ingredients, the present invention teaches a novel dosage unit option for transdermal and dermal absorption dosage units. A conventional dosage unit comprises a removable backing layer that is impervious to the pharmaceutical product to be administered, an adjoining layer having dissolved or microdispersed pharmaceutical product therein, a biologically suitable adhesive means by which the dosage unit adheres to the skin of a patient receiving the dosage, and an impermeable coating. The present invention contemplates a series of perforations or alternately, scoring lines, with purpose to divide the dosage unit into a series of dose specific segments. Thus the dosage unit patch may be used in its entirety for the full dosage, or in the alternative, may be separated along perforate or scored lines to reduce the dosage received by a predetermined amount. For example, a dosage unit patch may allow administration of 0.1 mg of a pharmaceutical product, but, in accordance with the present invention, may come in the form of four perforately attached segments each having a dosage of 0.025 mg. In this example, a physician may then prescribe the full 0.1 mg dosage, or, if the patient is unable to tolerate the full dosage, may prescribe any fractional dosage obtainable by separating the appropriate fractional dose from the total dosage patch. Fractional doses unused after separation may be used at a later time, thus reducing waste.

This invention further contemplates a method of administering a controlled amount of a pharmaceutical to the skin of a patient by dermal or transdermal absorption. The method includes the steps of providing an absorption dosage unit having a removable backing layer which is substantially impervious to the pharmaceutical to be administered. The dosage unit further includes a biologically acceptable adhesive layer for securing the dosage unit to the patient, a membranous layer permeable to the pharmaceutical and containing a measured amount of the pharmaceutical, a protective coating layer which is substantially impervious to the pharmaceutical, and means for dividing and severing said segmented dosage unit. Further steps include manually severing a pre-selected number of segments from the dosage unit, removing the backing layer from the pre-selected number of segments to expose the adhesive layer and membranous layer of each of the pre-selected number of segments, adhesively attaching the exposed segmented membranous layer to the skin of a patient and allowing the segmented membranous layer to remain adhesively attached to the skin of a patient for a predetermined amount of time.

DESCRIPTION OF THE DRAWINGS

FIG. 1 is a perspective view of the segmented dosage patch of the present invention showing four severably attached segments.

FIG. 2 is a top plan view of the segmented dosage patch of the present invention and showing perforations for severing the individual segments.

FIG. 2a is a top plan view of an alternate embodiment of the segmented dosage patch and showing surface scoring for severing the individual segments.

FIG. 3 is a cross sectional view of the dosage patch shown in FIG. 2 and taken along line 3—3 thereof.

FIG. 3a is a cross sectional view similar to the view shown in FIG. 3, but showing an alternate embodiment dosage patch having a layer with pharmaceutical product microdispersed thereon.

DETAILED DESCRIPTION

Figure 4:
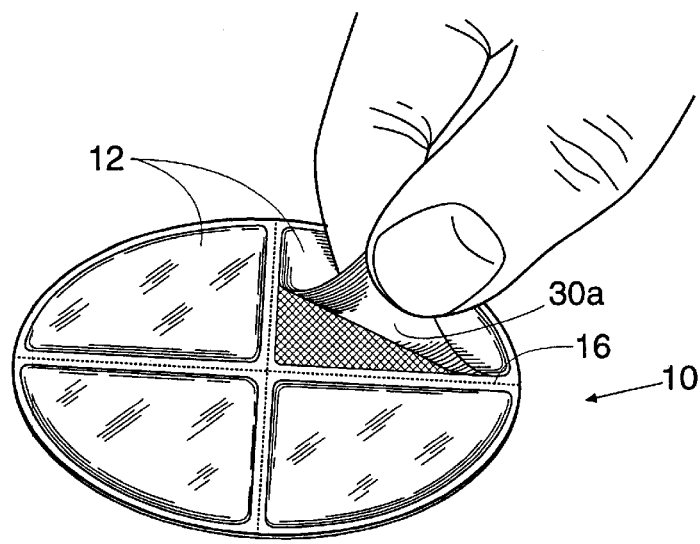
FIG. 4 is a perspective view of the segmented dosage patch and showing one segment thereof being separated from the backing layer.

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

The present invention is directed to an improved dermal or transdermal dosage unit having a pharmaceutical dispersed on a permeable membrane that is adapted to be applied directly to the skin of a patient (see FIG. 6) receiving the pharmaceutical product. The improvement resides principally in the severing and detachment means 14, as seen in FIGS. 1–5.

With reference to FIG. 1, the present invention, seen as a segmented dermal or transdermal dosage unit, is generally indicated by reference numeral 10. The dosage unit or patch 10 is divided into a plurality of independent segments 12, which may be separated from one another by way of severing means 14. The segmental dosage unit 10 is shown as divided into four segmented quadrants 12 but may be divided into any desired fractional configuration. The preferred embodiment severing means 14 is seen in FIG. 2 and is shown as series of perforations 16 extending through the dosage unit 10. While perforations 16 are the preferred embodiment, scored areas 18 may also be used (See FIG. 2*a*). It is to be understood that while perforations and scoring are disclosed in the present invention, other acceptable severing means is within the scope of this disclosure.

With reference to FIGS. 3 and 3*a*, the various layers 19 comprising the dosage unit 10 are seen. The layers 19 comprising the dosage unit 10 are typical to units such as these and preferably include an occlusive, removable backing layer 20, a permeable porous membrane 22 having two surfaces 30*a*, 30*b*, (see also FIG. 4), a pharmaceutical dosage layer 24 microdispersed on surface 30*b*, adhesive means 26 on the surface 30*a* of the porous membrane 22, and an impermeable coating 28.

The removable backing layer 20 is preferably substantially impervious to the pharmaceutical 24 to be delivered, and extends coextensively with the patch 10 prior to removal. In the preferred embodiment, seen in FIG. 3, the backing layer 20 is removably adhered to surface 30*a* of a permeable porous membrane 22 by way of a biologically acceptable adhesive means 26 on surface 30*a*. The adhesive 26 also serves to adhere the dosage unit 10 to the skin of the patient receiving the dosage (see FIG. 6) and may be over the entire surface 30*a* of the porous membrane 22, as seen in FIG. 3, or may define an adhesive free area (not shown). Any of the well-known dermatologically acceptable pressure-sensitive adhesives may be used in accordance with this invention, however the adhesive means 26 must additionally exhibit ability to allow pharmaceutical migration therethrough.

The permeable membranous material to be used in the permeable membrane layer 22 is known in the art and is best described as a plurality of conjoining porous particles which provide a supporting structure while providing a dispersion of microscopic sized interconnecting pores. In order to obtain optimal results, the membrane 22 used for a particular pharmaceutical should be chosen as having the configuration and pore size necessary to achieve the desired release rate for the pharmaceutical to be administered. In addition, the membrane 22 used must be chemically resistant to the pharmaceutical to be administered and non-toxic to the patient receiving the dosage unit 10.

The pharmaceutical dosage layer 24 may be in the form of a separate encapsulated layer shown in FIG. 3, or may be microdispersed on the surface 30*b* of the permeable membrane 22, as seen in FIG. 3*a*. The segmented dosage unit 10 of the present invention may be used to deliver any pharmaceutical having a set of desired properties. The properties necessary include the ability to be transdermally absorbed at a level sufficient to elicit the desired physiological response, and the ability to transverse the porous membrane 22 and the adhesive 26 attached thereto.

Figure 5:
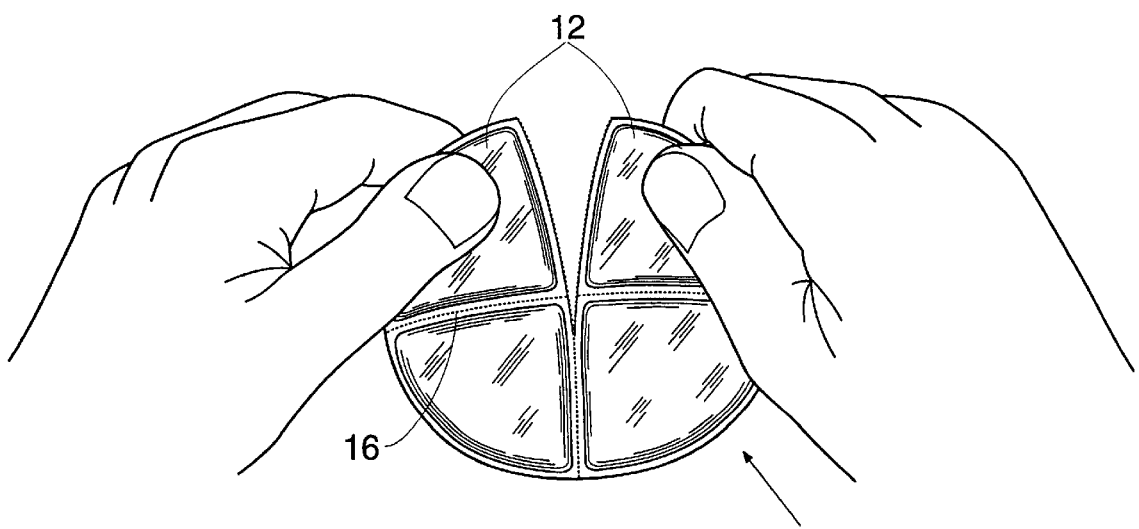
FIG. 5 is a perspective view of the segmented dosage patch and showing the patch, including the backing layer being severed into two segments.
Figure 6:
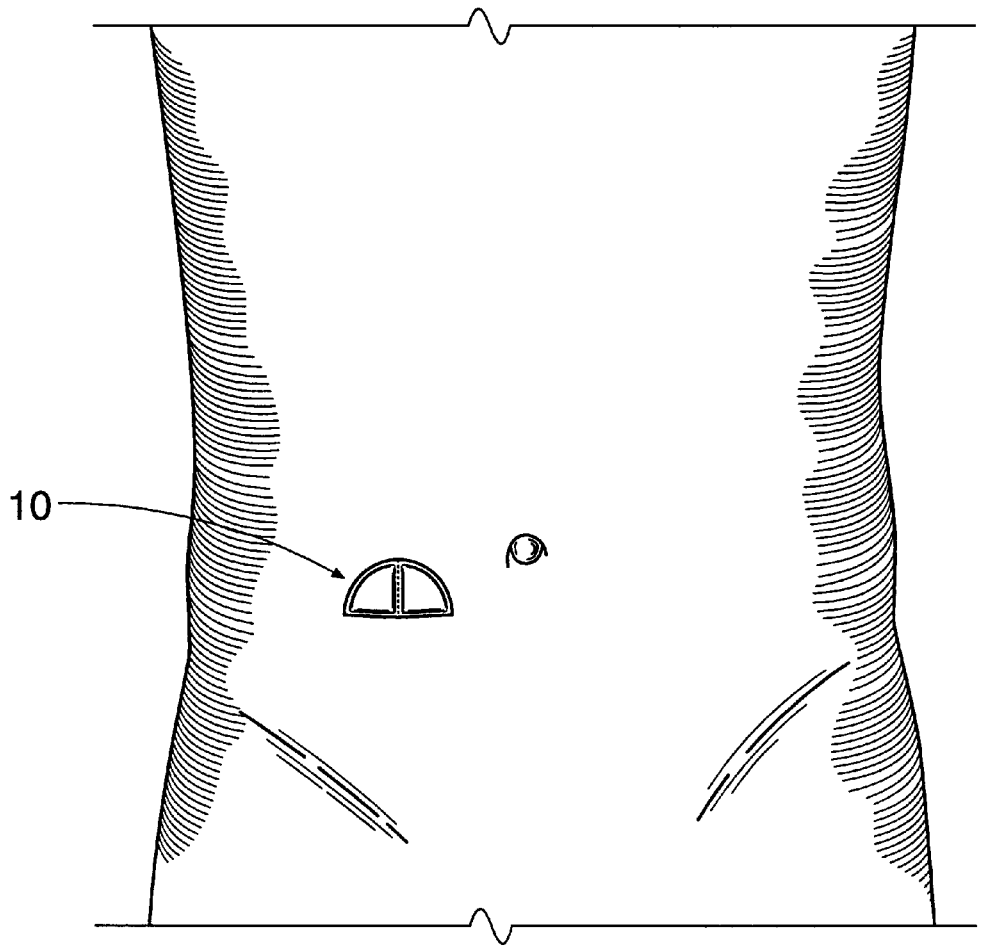
FIG. 6 is a perspective view of two segments of the patch affixed to a patient's torso.

The present invention contemplates independent segments 12 which may be severed from one another by employing severing means 14, such as perforations 16. The segments 12 may be severed in their entirety and through the layers 19, as seen in FIG. 5 to define the borders of adjoining segments 12. In this example, the fractionalized independent segments 12 are separated and ready for application or later use. The perforations 16 may also be utilized to sever at least one layer, as shown in FIG. 4, wherein the fractionalized independent segment 12 is removed from the backing layer 20 for immediate use by a patient while the conjoined segments 12 remain affixed to the backing layer 20 for later detaching and use.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A severable, relatively flat, segmented transdermal or dermal absorption dosage unit for administering a controlled amount of a pharmaceutical to a patient, said unit comprising:

a removable backing layer that is substantially impervious to said pharmaceutical;

a biologically acceptable adhesive layer for securing said dosage unit to said patient;

a layer containing a measured amount of said pharmaceutical;

a protective coating layer which is substantially impervious to said pharmaceutical; and severable perforations transversely extending through each of said layers.

2. The absorption dosage unit of claim 1 wherein said severable perforations define pre-selected segmental areas corresponding to fractional dosages of said pharmaceutical.

3. A method of administering a controlled amount of a pharmaceutical to the skin of a patient by dermal or transdermal absorption, said method including the steps of:

providing an absorption dosage unit, said unit having a removable backing layer which is substantially impervious to said pharmaceutical, a biologically acceptable adhesive layer for securing said dosage unit to said patient, a membranous layer permeable to said pharmaceutical and containing a measured amount of said pharmaceutical, a protective coating layer which is substantially impervious to said pharmaceutical, and severable perforations transversely extending through each of said layers;

manually severing a pre-selected number of segments from said dosage unit;

removing the backing layer from said pre-selected number of segments to expose said adhesive layer and said membranous layer of each of said pre-selected number of segments;

adhesively attaching said exposed segmented membranous layer to the skin of said patient; and allowing said segmented membranous layer to remain adhesively attached to the skin of said patient for a predetermined amount of time.

4. The method of claim 3 wherein said means for dividing and severing said dosage unit comprises perforations.

5. The dosage unit of claim 1 wherein said layer containing a measured amount of said pharmaceutical is a permeable membranous layer.

6. In a relatively flat, transdermal or dermal absorption dosage unit for administering a controlled amount of a pharmaceutical to a patient, the improvement comprising:

severable perforations transversely extending through each of said layers for dividing said dosage unit into a plurality of fractional dosage segments; and means for detaching said fractional dosage segments from said dosage unit.

7. The dosage unit of claim 6 wherein said means for dividing and detaching said dosage unit into said dosage segments comprises manually severable perforations.

8. The dosage unit of claim 6 wherein said means for dividing and detaching said dosage unit into said dosage segments comprises at least one manually severable score defining said fractional dosage segment.

9. The absorption dosage unit of claim 1 wherein said dividing and severing means comprises at least one manually severable score transversely extending through each of said layers and defining pre-selected segmental areas corresponding to fractional dosages of said pharmaceutical.

* * * * *